(12) United States Patent
Al-Qahtani

(10) Patent No.: US 8,877,494 B2
(45) Date of Patent: Nov. 4, 2014

(54) HUMAN CORNEAL EPITHELIAL CELL LINE PTA-120527

(71) Applicant: Ahmed H. Al-Qahtani, Irvine, CA (US)

(72) Inventor: Ahmed H. Al-Qahtani, Irvine, CA (US)

( * ) Notice: Subject to any disclaimer, the term of this patent is extended or adjusted under 35 U.S.C. 154(b) by 0 days.

(21) Appl. No.: 14/092,637

(22) Filed: Nov. 27, 2013

(65) Prior Publication Data

US 2014/0099355 A1 Apr. 10, 2014

Related U.S. Application Data

(63) Continuation-in-part of application No. 12/793,927, filed on Jun. 4, 2010.

(51) Int. Cl.
| | |
|---|---|
| *C12N 5/071* | (2010.01) |
| *C12N 5/07* | (2010.01) |
| *C12N 5/22* | (2006.01) |
| *C12N 5/10* | (2006.01) |
| *A61K 31/07* | (2006.01) |
| *A61K 33/10* | (2006.01) |
| *A61K 35/30* | (2006.01) |
| *A61K 31/351* | (2006.01) |
| *A61K 45/06* | (2006.01) |
| *A61K 31/4178* | (2006.01) |
| *A61K 31/382* | (2006.01) |
| *A61K 31/165* | (2006.01) |
| *A61K 38/18* | (2006.01) |
| *A61K 33/14* | (2006.01) |
| *A61K 31/341* | (2006.01) |
| *A61K 38/19* | (2006.01) |
| *A61K 47/38* | (2006.01) |
| *A61K 38/17* | (2006.01) |
| *A61K 9/00* | (2006.01) |

(52) U.S. Cl.
CPC .................. *A61K 35/30* (2013.01); *A61K 31/07* (2013.01); *A61K 33/10* (2013.01); *A61K 31/351* (2013.01); *A61K 45/06* (2013.01); *A61K 31/4178* (2013.01); *A61K 31/382* (2013.01); *A61K 31/165* (2013.01); *A61K 38/18* (2013.01); *A61K 33/14* (2013.01); *A61K 31/341* (2013.01); *A61K 38/19* (2013.01); *A61K 47/38* (2013.01); *A61K 38/1735* (2013.01); *A61K 9/0048* (2013.01)
USPC .......................... 435/371; 435/326; 435/366

(58) Field of Classification Search
CPC ... A61K 2300/00; A61K 35/33; A61K 35/30; A61K 38/18; A61K 38/1825; A61K 38/39; A61K 38/1709; C12N 5/0621; C12N 2501/11; C12N 2501/115; C12N 2501/235
See application file for complete search history.

(56) References Cited

U.S. PATENT DOCUMENTS

| | | | | |
|---|---|---|---|---|
| 5,703,047 | A * | 12/1997 | Wilson ........................ | 424/491 |
| 6,218,360 | B1 * | 4/2001 | Cintron et al. ................. | 514/9.4 |
| 6,372,494 | B1 * | 4/2002 | Naughton et al. ............ | 435/391 |
| 6,429,194 | B1 * | 8/2002 | Leahy et al. ................. | 514/20.8 |
| 6,976,997 | B2 * | 12/2005 | Noolandi et al. ............ | 623/5.14 |
| 7,332,470 | B2 * | 2/2008 | Fleiszig et al. ................ | 514/2.8 |
| 2004/0049268 | A1 * | 3/2004 | Noolandi et al. ............ | 623/5.14 |
| 2004/0229802 | A1 * | 11/2004 | Fleiszig et al. ................ | 514/12 |
| 2011/0206620 | A1 * | 8/2011 | Dana et al. ...................... | 424/43 |
| 2012/0141410 | A1 * | 6/2012 | Torfi ............................ | 424/85.2 |

* cited by examiner

*Primary Examiner* — Chang-Yu Wang
(74) *Attorney, Agent, or Firm* — Mandour & Associates, APC

(57) ABSTRACT

The present invention relates to topical ophthalmic compositions for treating or preventing epithelial lesions or ophthalmic disorders, including dry eye or keratoconjunctivitis sicca.

1 Claim, 2 Drawing Sheets

HUMAN CORNEAL EPITHELIAL CELL LINE PTA-120527

CROSS REFERENCE TO RELATED APPLICATION

This application is a continuation-in-part of U.S. application Ser. No. 12/793,927, filed Jun. 4, 2010.

BACKGROUND OF THE INVENTION

1. Field of the Invention

The present invention relates generally to ophthalmic compositions, and specifically to human conjunctiva-derived mucin compositions, including the use of such compositions in methods for the treatment of epithelial lesions of the eye and ophthalmic disorders.

2. Background Information

It has now been shown that the classic aqueous-dominated tear film model of dry eye has been replaced by the more probable concept of a mucin-dominated gel. This gel has its highest concentration of mucin at the epithelial surfaces of the cornea and conjunctiva, and the mucin concentration gradually decreases farther out into the tear film. In this model, the presence of mucin remains significant for the structure, stability and function of the entire tear film. Recent studies of the tear film using laser interferometry and confocal microscopy indicates that the human tear film is 30 to 40 microns thick, more than four times thicker than earlier estimates. Based on tear film physiology and clinical observations, tear film abnormalities are commonly designated by focus on a specific deficiency, such as an aqueous tear deficiency, keratoconjunctivitis sicca (KCS), a mucin deficiency, a lipid abnormality, an impaired lid function, or an epitheliopathy. Although clinically useful, the simplistic concept of a lack of one component of the tear film as the cause of dry eye has given way to a much more sophisticated view of ocular surface disease that involves: (1) the health and regulation of the various glands contributing secretions to the tear film, (2) changes in the tear film itself, such as in osmolality and content of inflammatory mediators, and (3) what is viewed as a sort of "final common pathway," the subsequent changes to the ocular surface. In fact, many clinicians and authors prefer the term "ocular surface disease" over "dry eye," for it is change to the ocular surface, whatever the original cause that results in the significant signs and symptoms of dry eye. The discomfort of ocular surface disease is expressed in ocular symptoms, such as dryness, grittiness, burning, soreness or scratchiness, with variation among individuals. These symptoms can also be exacerbated by factors such as environmental conditions and contact lens wear. The combination of varying clinical signs and symptoms has also been termed dry eye syndrome.

In the human eye, the secretory mucins MUC2 and MUC5AC have been detected (via transcripts at the nucleic acid level) from conjunctival isolates, and only MUC5AC has been localized to conjunctival goblet cells. Unique characteristics of normal human secreted ocular mucins are their wide size range and short oligosaccharide side chains.

The transmembrane mucin MUC1 is associated with the cell membranes of the entire corneal and conjunctival epithelial surface, except the goblet cells. Another transmembrane mucin is the mucin MUC4, which is associated with the cell membranes of the entire conjunctival epithelial surface, except the goblet cells.

In a mild to moderate dry eye, the goblet cell density is not significantly reduced, indicating that MUC5AC is most likely to be produced normally, in quantities sufficient to be spread over the entire ocular surface. However, localized early ocular surface changes resulting from dryness, such as that revealed by fluorescein or rose bengal staining, can be seen in the epithelia of the corneal and conjunctival surfaces. This localized damage to the ocular surface indicates that even marginal dryness might have a significant effect on the presence of functional MUC1 on the surface of the ocular epithelium. Since one of the proposed functions of MUC1 is to help the other, more abundant gel-forming ocular mucins adhere to the ocular surface, a paucity of MUC1 might significantly affect the stability of the tear film, even in the presence of an abundance of MUC5AC secreted by the conjunctival goblet cells. There is some early evidence that with the progression of changes to the ocular surface mucins associated with dry eye, as detected by immunohistochemical methods, the goblet cells themselves try to make up for the lack of normal expression of MUC1 by the rest (non goblet cells) of the corneal and conjunctival surface epithelium, and begin expressing a MUC1-like molecule in their secretions.

The secreted ocular mucins are relatively large molecules, and have a significant role in the gel-forming nature of the tear film. The model of the greater part of the tear film being a highly hydrated mucus gel, rather than simply a watery aqueous layer, is becoming increasingly accepted. The viscoelasticity of the tear film derives from the specific structure and gel-forming properties of the ocular mucins, and allows the tear film to absorb the shear force of the blink, which would otherwise irritate and damage the ocular surface. The transmembrane mucin, on the other hand, serves more as a protective layer on the actual cellular surface of the ocular epithelium, functioning to directly protect and lubricate the ocular surface, as well as to anchor the highly hydrated gel (mucus) of the tear film gel forming mucins, thereby assisting in the spreading and stability of the tear film over the ocular surface.

The importance of mucin in the natural tear fluid as a wetting agent, viscoelastic gel former, lubricant and barrier to bacterial adhesion has largely been reported. Limited success with so many various synthetic and substitute polymers indicate that supplementing the tear fluid with a compatible mucin from an exogenous source would appear to be a more direct and preferred method for addressing dry eye conditions. Part of the problem in the development of ocular surface changes in dry eye disease may be the dehydration of the mucus gel and subsequently the mucin layer of the cellular surface. Supplementing the tear fluid with mucin in an aqueous solution would be expected to help maintain the natural surface mucin layer of the eye by both the addition of the additional mucin molecules and the hydration provided by the aqueous vehicle.

The belief that the tear film is aqueous based and the ocular surface changes seen in Sjogren's syndrome are due to desiccation, cause eye care practitioners to water the dry eye. However, studies show that, as stated above, the tear film is dominated by mucin and not water. The human tear film is not a 7-10 pm thin film, but a 30-35 pm thick mucin gel. Bicarbonate may be critical to forming this gel as it is in forming the bicarbonate mucin gel that protects the stomach from autodigestion. The hallmark of the aqueous deficient dry eye, rose bengal staining of the conjunctiva, is not produced by desiccated cells, but is due to a deficiency in the protective mucin gel. The ocular surface changes in dry eye include conjunctival squamous metaplasia, loss of integrity of cell membranes and junctional structures (fluorescein staining), and loss of the integrity of the mucin layer (rose bengal staining). Rose bengal staining and squamous metaplasia are not improved by the frequent application of non-preserved preparations. Bicarbonate and electrolyte solutions promote recovery of barrier function and ultrastructure in damaged ocular surface cells and increase corneal glycogen and goblet cell density. These solutions, however, do not totally reverse ocular surface disease seen in Sjogren's syndrome. Even with the addition of electrolytes and bicarbonate to artificial tears, watering the dry eye is not enough.

It has been found that the application of autologous serum improved fluorescein and rose bengal scores and squamous metaplasia. This treatment also resulted in significant upregulation of MUC-1 in conjunctival epithelial cell cultures. It is believed that the epidermal growth factor (EGF), vitamin A, and transforming growth factor B (TGF-β) found in serum represent critical components missing from the tears of patients with Sjogren's syndrome.

Studies have shown that some cytokines play an important role in the regulation of proliferation, differentiation, and maturation of the ocular surface epithelium, while the cytokines may be harmful. Experimental studies demonstrate that EGF and hepatocyte growth factor (HGF), which are present in human tears and secreted by the lacrimal gland, are important in corneal wound healing. Both also increase as aqueous tear production increases. TGF-α and TGF-β are found in human tears. Both are probably involved in corneal epithelial cell growth and differentiation. Retinol, also secreted by the lacrimal gland and found in the tear film, is necessary for the maintenance of healthy ocular surface epithelium. Not only may the tear film of patients with Sjogren's syndrome be missing critical components, tears may actually contain substances that lead to ocular surface injury. Cytokines may be produced in or by the lacrimal gland in response to inflammation. These factors, delivered to the ocular surface by the tear fluid, may lead to inflammation of the ocular surface. mRNA for interleukins IL-1 and IL-6 has been detected in the lacrimal glands of autoimmune female MRL/lpr mice. Increased levels of IL-1 induce keratinocyte apoptosis and metalloproteinase expression, where IL-6 induces lymphocytic differentiation.

In addition, cells also produce extracellular vesicles. Extracellular vesicles, or exosomes, have emerged as potent vehicles for cell-to-cell communication since the discovery that they contain functional mRNA, miRNA, DNA, and protein molecules that can be taken up by target cells. The generic information contained in exosomes can influence or even direct the fate of a target cell, for example, by triggering target cell activation, migration growth, differentiation, de-differentiation, or by promoting apoptosis or necrosis. As such, exosomes can provide additional cell factors which assist in the regulation of proliferation, differentiation, and maturation of the ocular surface epithelium.

In Sjogren's syndrome, reflex tearing decreases with increased lymphocytic infiltration of the lacrimal gland. Reflex tearing flushes debris from the ocular surface, dilutes substances in the tear film, and delivers higher amounts of certain cytokines to the ocular surface. The loss of reflex tearing results in reduced tear clearance causing prolonged retention of substances in the tear film. It is likely that the loss of reflex tearing also results in the lack of delivery of cytokines and retinol critical to the growth and differentiation of ocular surface epithelial cells.

The upregulation of MUC-1 suggests there are substances in serum, which promote reformation of the mucin gel, and, therefore, resolution of rose bengal staining. It is believed that similar substances, that are important in the maintenance of the mucin gel, are probably missing in the Sjogren's dry eye.

Some have speculated on the use of serum tears. It has also been suggested that serum tears, alone, may not be sufficient to treat dry eye. For example, it has been found that the presence of cytokines and retinol are critical for the growth, differentiation, and wound healing of the ocular surface. Artificial tears flush out debris, dilute substances trapped in the tear film, and increase tear clearance. Artificial tears do not, however, provide all the factors critical for the maintenance and repair of the ocular surface.

SUMMARY OF THE INVENTION

The present invention provides a method of treating dry eye by topically administering to the eye a human conjunctiva-derived mucin containing composition, which derived mucin is similar to those of the transmembrane mucin expressed on the ocular surface epithelium, and to the gel-forming mucins secreted by the goblet cells, in addition, said composition may comprise a fraction enriched with exosomes. The compositions of this invention protect the ocular surface from dryness and absorb shear forces of the blink, and assist the eye's own secreted gel forming mucins (predominantly MUCS) in maintaining their viscoelastic properties and ensuring structure and stability of the tear film, thereby slowing or preventing the changes to the ocular surface seen in dry eye conditions.

In one embodiment, a method for treating dry eye or keratonconjunctivitis sicca (KCS) is disclosed including topically administering an ophthalmic composition comprising conditioned media, or concentrate of said media, from cultured corneal epithelial cells in combination with a pharmaceutically acceptable carrier to the ocular surface or immediate vicinity of an eye of a subject in need thereof, where the cultured corneal epithelial cells do not contain goblet cells.

In one aspect, the conditioned media, or concentrate of the media, is from a cell line designated as ATCC Accession No. PTA-120527.

In another aspect, the composition is applied to the ocular surface of the eye. In one aspect, the composition is applied to a region of the eye adjacent the ocular surface.

In one aspect, the composition includes one or more human growth factors and an enriched exosome fraction isolated from the cultured corneal epithelial cells.

In another aspect, the one or more growth factors include EGF or TGF-β and combinations thereof. In a related aspect, the one or more growth factors include GM-CSF, IL-15, IL-1a, IL-2, IL-4, IL-5, IL-6, IL-7, IL-8, MCP-1, TNFα, FGF-2, Flt-3, PDGF-AA, TGF-β1, TGF-β2, and TGF-β3, and combinations thereof. In a further related aspect, the composition includes about 3.0-5.0 mg/ml mucin, about 0.3-0.6 pg/ml GM-CSF, about 0.09-0.2 pg/ml IL15, about 0.17-0.3 pg/ml IL-1a, about 0.095-1.6 pg/ml IL-2, about 0.3-0.6 pg/ml IL-4, about 1.68-2.8 pg/ml IL-6, about 0.06-0.1 pg/ml IL-7, about 0.17-0.3 pg/ml IL-8, about 1.3-2.3 pg/ml MCP-1, about 0.059-0.1 pg/ml TNF-α, about 2.3-4.0 pg/ml FGF-2, about 1.1-2.0 pg/ml Flt-3, about 9.5-16 pg/ml PDGF-AA, about 0.65-1.035 ng/ml TGF-β1, about 28-46 pg/ml TGF-β3, and about 85-130 pg/ml TGF-β2.

In one aspect, the ophthalmic composition is provided via elution from a contact lens containing the composition.

In another aspect, the ophthalmic composition includes an antibiotic. In a related aspect, the antibiotic includes bacitracin, neomycin, gentamicin, tobramycin, ciprofloxicin, cefazolin, chloramphenicol, ofloxicin, vancomycin, ceftazidime, and amikacin, and a combination thereof. In a further related aspect, the ophthalmic composition further includes a combination comprising bacitracin and neomycin.

In embodiments, a topical ophthalmic composition for treating dry eye or keratonconjunctivitis sicca (KCS) is disclosed including conditioned media or cell free extract or concentrate thereof from cultured epithelial corneal cells, where the cultured corneal epithelial cells do not contain goblet cells, and a water-soluble viscosity building agent, where the conditioned media is generated by incubating a nutrient medium with the cells under conditions which promote secretion of at least one human growth factor into the nutrient medium.

In one aspect, the cell free extract, or concentrate thereof, is from a cell line designated as ATCC Accession No. PTA-120527.

In another aspect, the water-soluble viscosity building agent includes guar gum, gum tragacanth, gelatin, starch derivatives, polymeric glycols, hydroxyethylcellulose, hydroxypropylcellulose, methylcellulose, hydroxyropylmethylcellulose, and carboxymethylcellulose.

In one aspect, the water-soluble viscosity building agent is carboxymethylcellulose. In a related aspect, the composition further comprises retinol. In another aspect, the ophthalmic composition further includes a bacteriological preservative. In a related aspect, the bacteriological preservative includes benzalkonium chloride, thimerosal, phenylmercuric nitrate, chlorobutanol, and sorbicacid.

In another aspect, the ophthalmic composition further includes a chelating agent.

In one aspect, the growth factor includes GM-CSF, IL-15, IL-1a, IL-2, IL-4, IL-5, IL-6, IL-7, IL-8, MCP-1, TNFα, FGF-2, Flt-3, PDGF-AA, TGF-β1, TGF-β2, and TGF-β3, or combinations thereof and an enriched exosome fraction isolated from the cultured corneal epithelial cells.

In one aspect, the composition further includes bicarbonate.

In another aspect, the composition includes about 3.0-5.0 mg/ml mucin, about 0.3-0.6 pg/ml GM-CSF, about 0.09-0.2 pg/ml IL15, about 0.17-0.3 pg/ml IL-1a, about 0.095-1.6 pg/ml IL-2, about 0.3-0.6 pg/ml IL-4, about 1.68-2.8 pg/ml IL-6, about 0.06-0.1 pg/ml IL-7, about 0.17-0.3 pg/ml IL-8, about 1.3-2.3 pg/ml MCP-1, about 0.059-0.1 pg/ml TNF-α, about 2.3-4.0 pg/ml FGF-2, about 1.1-2.0 pg/ml Flt-3, about 9.5-16 pg/ml PDGF-AA, about 0.65-1.035 ng/ml TGF-β1, about 28-46 pg/ml TGF-β3, and about 85-130 pg/ml TGF-β2.

In one aspect, the composition includes an antibiotic. In a related aspect, the antibiotic includes bacitracin, neomycin, gentamicin, tobramycin, ciprofloxicin, cefazolin, chloramphenicol, ofloxicin, vancomycin, ceftazidime, and amikacin and a combination thereof. In a related aspect, the composition further includes a combination comprising bacitracin and neomycin.

In embodiments, a kit is disclosed including at least one container; an ophthalmic composition including conditioned media or cell free extract or concentrate thereof from cultured corneal epithelial cells and a water-soluble viscosity building agent, where the conditioned media or cell free extract or concentrate thereof is from a cell line designated as ATCC Accession No. PTA-120527; instructions which provide methods of mixing the composition and water-soluble building agent and/or methods of applying the composition to treat or prevent dry-eye.

In one aspect, the ophthalmic composition further includes an enriched exosome fraction isolated from the cultured corneal epithelial cells. In another aspect, the at least one container is a contact lens container.

In one aspect, the ophthalmic composition includes about 3.0-5.0 mg/ml mucin, about 0.3-0.6 pg/ml GM-CSF, about 0.09-0.2 pg/ml IL15, about 0.17-0.3 pg/ml IL-1a, about 0.095-1.6 pg/ml IL-2, about 0.3-0.6 pg/ml IL-4, about 1.68-2.8 pg/ml IL-6, about 0.06-0.1 pg/ml IL-7, about 0.17-0.3 pg/ml IL-8, about 1.3-2.3 pg/ml MCP-1, about 0.059-0.1 pg/ml TNF a, about 2.3-4.0 pg/ml FGF-2, about 1.1-2.0 pg/ml Flt-3, about 9.5-16 pg/ml PDGF-AA, about 0.65-1.035 ng/ml TGF-β1, about 28-46 pg/ml TGF-β3, and about 85-130 pg/ml TGF-β2.

In another aspect, the water-soluble viscosity building agent includes guar gum, gum tragacanth, gelatin, starch derivatives, polymeric glycols, hydroxyethylcellulose, hydroxypropylcellulose, methylcellulose, hydroxyropylmethylcellulose, and carboxymethylcellulose.

In one aspect, the kit includes at least one pair of contact lenses.

In another aspect, the ophthalmic composition further includes a bacteriological preservative. In a related aspect, the bacteriological preservative includes benzalkonium chloride, thimerosal, phenylmercuric nitrate, chlorobutanol, and sorbicacid.

In one aspect, the ophthalmic composition further includes a chelating agent.

In another aspect, the ophthalmic composition further includes an antibiotic. In a related aspect, the antibiotic includes bacitracin, neomycin, gentamicin, tobramycin, ciprofloxicin, cefazolin, chloramphenicol, ofloxicin, vancomycin, ceftazidime, and amikacin and a combination thereof. In a further related aspect, the ophthalmic composition further contains a combination of bacitracin and neomycin.

In embodiments, a human corneal epithelial cell line is disclosed, where the line is ATCC Accession No. PTA-120527.

DETAILED DESCRIPTION OF THE INVENTION

Figure 1:
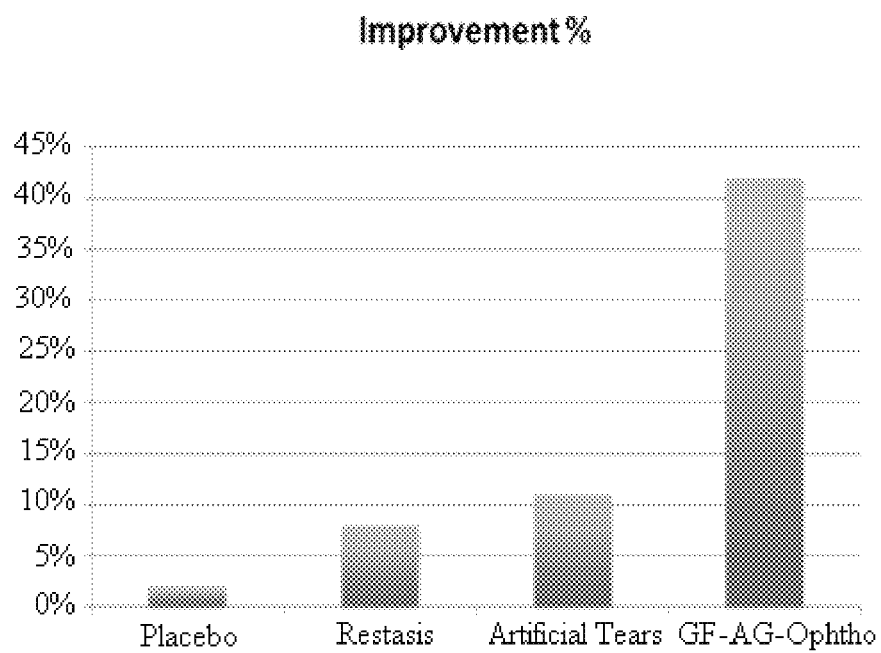
FIG. 1 shows the improvement of dry eye in patients receiving condition media-containing ophthalmic solution (GF-AG-Ophtho; bar 4). Treatment was compared to placebo (pharmaceutical carrier; bar 1), RESTASIS™ (0.05% cyclosporine ophthalmic emulsion) (bar 2), and artificial tears (bar 3).

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a growth factor" includes one or more growth factors, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein, "conditioned media," including grammatical variations thereof, means culture media containing biologically active components obtained from previously cultured cells or tissues that have released into the media substances affecting certain cell functions. In related aspect, cell free extracts of conditioned media include, but are not limited to, concentrates and diluates of such media.

As used herein, "administering," including grammatical variations thereof, means a method of giving a dosage of a pharmaceutical or therapeutic composition to a subject. In a related aspect, the subject is mammalian, preferably a human.

As used herein, "an amount sufficient to treat," including grammatical variations thereof, means the amount of a compound required to improve, inhibit, or ameliorate a condition of a subject, or a symptom of a disorder, in a clinically relevant manner. Any improvement in the subject is considered sufficient to achieve treatment.

As used herein, "mucin" means a biologically active, glycosylated polypeptide that is substantially identical to MUC1, MUC2, MUC3A, MUC3B, MUC4, MUC5AC, MUC5B, MUC6, MUC7, MUC8, MUC9, MUC11, MUC12, MUC13, MUC15, MUC16, MUC17, MUC18, MUC19, or MUC20. Carbohydrates may contribute, e.g., 50-90% of the total molecular weight of the mucin. A mucin is biologically active if it exhibits a biological activity of a naturally-occurring mucin glycoprotein, e.g., the ability to form mucus.

As used herein, "therapeutic agent," including grammatical variations thereof, means any agent that produces a preventative, healing, curative, stabilizing, or ameliorative effect.

As used herein, "treating," including grammatical variations thereof, means administering a pharmaceutical or therapeutic composition for prophylactic and/or therapeutic purposes. Prophylactic treatment may be administered, for example, to a subject who is not yet ill, but who is susceptible to, or otherwise at risk of, a particular disorder. Therapeutic treatment may be administered, for example, to a subject already suffering from a disorder in order to improve or stabilize the subject's condition.

As used herein, a "pharmaceutical acceptable carrier" is a pharmaceutically acceptable solvent, suspending agent or vehicle for delivering the ophthalmic composition to the animal or human. The carrier may be liquid or gel and is selected with the planned manner of administration in mind.

As used herein "exosomes" are defined as cell-derived vesicles that are present in many and perhaps all biological fluids, including blood, urine, tears, and cultured medium of cell cultures, possessing a diameter of between about 30 to about 100 nm, which diameter is larger than LDL, but much smaller than, for example, red blood cells. Exosomes may be released from the cell when multivesicular bodies fuse with the plasma membrane or they may be released directly from the plasma membrane.

As used herein "enrich", including grammatical variations thereof, means a process to increase the proportion of a desirable ingredient in a final product over that observed for the un-processed initial product.

An ophthalmic procedure, e.g., radial keratotomy, astigmatic or arcuate keratotomy, laser thermokeratoplasty, conductive keratoplasty, photorefractive keratectomy (PRK), phototherapeutic keratectomy, photoastigmatic refractive keratectomy, hyperopic photorefractive keratectomy, presbyopic photorefractive keratectomy, laser-assisted in situ keratomileusis (LASIK), hyperopic-LASIK, epi-LASIK, intra-LASIK, wavefront-LASIK, laser-assisted subepithelial keratomileusis, phakic intraocular lens implant, intraocular contact lens implant, refractive lens exchange, cataract extraction and intraocular lens implant, intracorneal ring implant, scleral expansion, or limbal relaxing incision, may result in an epithelial lesion.

An ophthalmic disorder may affect any part of the eye, e.g., the cornea, the sclera, the retina, the conjunctiva, the ciliary body, the posterior chamber, or the anterior chamber. In some embodiments, the ophthalmic disorder affects the cornea, e.g., the corneal epithelium, or the conjunctiva. Ophthalmic disorders that may be associated with epithelial lesions or impaired mucin function include, e.g., superficial punctate keratitis, corneal ulcer, herpes simplex keratoconjunctivitis, ophthalmic herpes zoster, phlyctenular keratoconjunctivitis, keratoconus, conjunctiva, keratoconjunctivitis sicca (dry eyes), ocular inflammation, corneal ulcers, and cicatricial pemphigoid. Ophthalmic disorders may be caused by viruses (e.g., adenoviruses or herpes simplex virus), blepharitis, keratitis sicca, trachoma, corneal foreign bodies, ultraviolet light exposure (e.g., welding arcs or sunlamps), contact lens overwear, systemic drugs (e.g., adenine arabinoside), topical drugs, bacteria, protozoa, fungi, or by a hypersensensitive reaction to a known or unknown antigen. Physical eye trauma can also result in an ophthalmic disorder. Physical trauma to the eye includes an abrasion to the cornea (e.g., caused by a foreign body), perforation of the cornea (e.g., caused by a blunt injury that disrupts the continuity of the cornea), chemical burns to the cornea (e.g., exposure to NaOH), or through surgical procedures (e.g., corneal transplants and intraocular injections). The ophthalmic disorder generally results in damage and disruption of eye function or structure. For example, the disorder may cause the corneal epithelium to tear, may cause necrosis of the cornea, may cause corneal ulcers, or may damage the conjunctiva.

The present invention relates to topical therapeutic and/or prophylactic formulations for treating epithelial lesions of the eye or ophthalmic disorders, comprising a conditioned medium from corneal cell cultures. The cells are preferably for mammalian sources, preferably human, to reduce the risk of an immune response. In one embodiment of the present invention, cultures of primary human corneal cells or primary conjunctiva cells are used to condition the nutrient medium in which they are bathed. Medium conditioned by such cell cultures contain a variety of naturally secreted proteins, including biologically active growth factors.

Growth factors, such as transforming growth factor-B, also known in the art as TGF-B, are induced by certain stress proteins during wound healing. Two known stress proteins are GRP78 and HSP90. These proteins stabilize cellular structures and render the cells resistant to adverse conditions. The TGF-B family of dimeric proteins includes TGF-β1, TGF-β2, and TGF-β3 and regulates the growth and differentiation of many cell types. Furthermore, this family of proteins exhibits a range of biological effects, stimulating the growth of some cell types and inhibiting the growth of other cell types. TGF-β has also been shown to increase the expression of extracellular matrix proteins including collagen and fibronectin and to accelerate the healing of wounds.

The growth factors that are derived from the above cell cultures include, but are not limited to, GM-CSF, IL-15, IL-1a IL-2, IL-4, IL-5, IL-6, IL-7, IL-8, MCP-1, TNFα, FGF-2, Flt-3, PDGF-AA, TGF-β1, TGF-β2, TGF-β3.

The cells may be readily isolated by disaggregating an appropriate eye or tissue which is to serve as the source of the cells. This may be readily accomplished using techniques known to those skilled in the art. For example, the tissue can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase and the like. Mechanical disruption can also be accomplished by a number of methods including, but not limited to, the use of grinders, blenders, sieves, homogenizers, pressure cells, or sonicators to name but a few. For a review of tissue disaggregation techniques, see Freshney, Culture of Animal Cells: A Manual of Basic Technique, 2d Ed., A. R. Liss, Inc., New York, 1987, Ch. 9, pp. 107-126, which is hereby incorporated by reference in its entirety.

Once the tissue has been reduced to a suspension of individual cells, the suspension can be fractionated into subpopulations from which the cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, Culture of Animal Cells: A Manual of Basic Techniques, 2d Ed., A. R. Liss, Inc., New York, 1987, Ch. 11 and 12, pp. 137-168, which is hereby incorporated by reference in its entirety.

The cells utilized to prepare the conditioned medium useful in the method of present invention may be cultured in accordance with disclosed embodiments by any means known in the art.

In some embodiments of the present invention, the growth factor-rich conditioned media may be diluted, concentrated and/or preserved prior to combining it with the variety of formulations for topical application to the eye of a subject in need thereof.

Concentration may be accomplished by any conventional methods known in the art, including for example, freeze-drying, vacuum-drying, evaporation, and the like. Moreover, particular growth factors may be concentrated by affinity chromatography or other conventional methods for protein/peptide purification. Dilution methods may include addition of deionized water. Preservation methods may include freeze-drying, spray-drying, foam-drying, and the like. In one embodiment, the medium is filtered with a 7 micron filter, then preservatives and other ingredients and/or supplements are added to the medium, and the medium is stored in a refrigerator. In addition, the conditioned medium may be subjected to further processing, e.g., affinity chromatography, to differentially concentrate or remove certain medium components.

Following removal of the cell conditioned medium, it may be necessary to further process the resulting supernatant. Such processing may include, but is not limited to, centrifugation, product isolation and purification, dilution of the media or concentration of the media by a water flux filtration device or by defiltration using the methods described in Cell & Tissue Culture Laboratory Procedures, supra, pp 29 D:0.1-29D:0.4, which is hereby incorporated by reference in its entirety.

The conditioned medium may be further processed for product isolation and purification to remove unwanted components. The methods used for product isolation and purification so that optimal biological activity is maintained will be readily apparent to one of ordinary skill in the art. For example, it may be desirous to purify a growth factor, regulatory, factor, and the like. Such methods include, but are not limited to, gel chromatography (using matrices such as Sephadex) ion exchange, metal chelate affinity chromatography with an insoluble matrix such as cross-linked agarose, HPLC purification and hydrophobic interaction chromatography of the conditioned media. Such techniques are described in greater detail in Cell & Tissue Culture; Laboratory Procedures, supra. Of course, appropriate measures may be taken to maintain sterility. Alternatively, sterilization may be necessary and can be accomplished by methods known to one of ordinary skill in the art, such as, for example, heat and/or filter sterilization taking care to preserve the desired biological activity.

In one embodiment, the media is filtered or centrifuged to prevent cell inclusion. It may then be diluted, e.g., with a phosphate buffer solution (PBS) or deionized water, if the growth factor concentrations are too high. Alternatively, the conditioned medium may be concentrated if the growth factor levels are not sufficiently high. The diluted or concentrated media may then be combined with an ophthalmically-acceptable vehicle, e.g. purified water, or an aqueous isotonic solution.

The pharmaceutical composition may be sterile and formulated in unit dosage form. The composition may be formulated for targeted delivery or extended release.

The conditioned media used in the method and compositions of the present invention may be prepared using dissected anterior segments of the eye (excluding goblet cells), where the segments are transferred to an appropriate media, including but not limited to Dulbecco's modified Eagles medium (DMEM), Roswell Park Memorial Institute medium (RPMI), and Eagle's Minimal Essential Medium (EMEM), which may be supplemented with serum (e.g., adult, newborn and fetal bovine serum, human serum, and the like), and an antibiotic (e.g., gentamicin and amphotericin B). Anterior eye components, for example, iris-ciliary body, lens, and corneal endothelium, including goblet cells, are removed, and the remaining tissue dissected into three zones, i.e. the central cornea, peripheral cornea and limbus. Cell may be treated with enzymes or chelating agents for tissue dissociation (e.g., trypsin and EDTA) and components of interest (i.e., the central and peripheral corneal) may be segregated by hydrodynamic methods (e.g., low speed centrifugation). The resulting epithelial sheets may be further dissociated by additional treatment with enzymes/chelating agents. The three isolated cell types may be cultured in an appropriate media and incubated, for example, at 37° C., 95% humidity, and 5% $CO_2$. The media may be changed regularly, for example, every 2 days, every 3 days, every 4 days, every 5 days, or every 6 days, depending on type of media used. Cells may be further cultured or processed for freezing at 60-70% confluence. The conditioned media is collected for formulation into the topical ophthalmic composition when the confluency reaches about 95-96%, about 95-97%, about 95-98%, about 95-99%, or about 95-100%. Cell density may be determined by any means known in the art.

In one aspect, corneal epithelial cells may be used, as they are devoid of goblet cells. For example, corneas may be excised and the posterior half stripped away. The anterior half may then be incubated at 35° C. either in culture medium containing 1.2 units (U) Dispase II/ml (Boehringer Mannheim; Indianapolis, Ind.) for 30, 45, or 60 min, or in Hank's Balanced Salt Solution without $Ca^{2+}$ or $Mg^{2+}$ but with 2.5 mM EDTA (tetrasodium) for 1 hr or 2 hr. The epithelial sheet may then be removed by gentle teasing with a pair of jeweler's forceps. The resulting free epithelial sheet and remnant stroma may then be rinsed three times in culture medium. Once separated from the remnant stroma cells, the resulting corneal epithelial sheets may be further dissociated by additional treatment with enzymes/chelating agents and cultured as recited above.

In another aspect, conjunctiva epithelial cells may be isolated as follows. Human conjunctival tissue is aseptically dissected and rinsed in phosphate buffered saline (PBS). The tissue may then be treated with dispase (Collaborative Research, Bedford, Mass.) at 10 U/ml in 50% Hank's buffered salts and keratinocyte basal medium (KGM; Clonetics, San Diego, Calif.), containing 0.05 mM calcium, at 4° C. for 24-48 h. Complete KGM may be prepared by adding 30 µg/ml of bovine pituitary extract, 0.5 µg/ml hydrocortisone, 0.05 µg/ml amphotericin B and 50 µg/ml gentamicin, 5 µg/ml insulin, 10 µg/ml transferrin, and 0.05 mM calcium chloride. After incubation with dispase, the slightly yellow conjunctival epithelium may be removed with a scalpel from the white connective tissue. The epithelium may then be gently dissociated to generate individual cells and washed in Dulbecco's modified Eagle medium (DMEM) containing 10% fetal bovine serum using a centrifugation (280×g/10 min)/re-suspension procedure. The cell pellet may then be re-suspended in a low calcium (0.05 mM) KGM, plated into T75 flasks (collagen type IV coated), and incubated at 37° C. under a humidified atmosphere of 95% air and 5% $CO_2$. The resulting conjunctiva epithelial cells may then be cultured as recited above.

In one aspect, deposit of human corneal epithelial cells designated AQHCEC-48Z has been made with the American Type Culture Collection ("ATCC"), 10801 University Blvd., Manassas, Va. on Aug. 8, 2013, having ATCC Accession No. PTA-120527.

The deposit was made in accordance with the terms and provisions of the Budapest Treaty. All restrictions on the availability to the public of the materials so deposited will be irrevocably removed upon the granting of the patent. The cells will be maintained for a term of at least thirty (30) years and at least five (5) years after the most recent request for the furnishing of a sample of the deposit is received by the depository, and at least beyond the enforceable life of the patent(s) for which the deposit was made, whichever is longer.

The conditioned media may be formulated into a topical ophthalmic composition for use in the method of the invention using a viscosity builder blended with a solution of physiological salts (e.g., Ringer's solution). The resulting blended suspension may be transferred into an appropriate container, where the solution may be sterilized before or after transfer. The sterilized suspension is then combined with the cell supernatant (i.e., conditioned media) and stored in an appropriate container. The amount of conditioned media in the composition may be present at a final concentration of about 35-50% (v/v), about 50-60% (v/v), or about 60-65% (v/v). In one embodiment, the amount of conditioned media in the composition is about 60-65% (v/v). The concentration of mucin in the final composition may be about 0.1-0.2% (w/v), about 0.2-0.3% (w/v), about 0.3-0.4% (w/v), or about 0.4-0.5% (w/v) ocular surface mucin (e.g., MUC1, MUC4, and MUC16). In one embodiment, the final concentration of mucin in the composition is about 0.5% (v/v). The amount of mucin in the media or composition may be determined by standard methods known in the art (for example, but not limited to, ELISA).

In one aspect, the composition includes about 3.0-5.0 mg/ml mucin, about 0.3-0.6 pg/ml GM-CSF, about 0.09-0.2 pg/ml IL15, about 0.17-0.3 pg/ml IL-1a, about 0.095-1.6 pg/ml IL-2, about 0.3-0.6 pg/ml IL-4, about 1.68-2.8 pg/ml IL-6, about 0.06-0.1 pg/ml IL-7, about 0.17-0.3 pg/ml IL-8, about 1.3-2.3 pg/ml MCP-1, about 0.059-0.1 pg/ml TNF a, about 2.3-4.0 pg/ml FGF-2, about 1.1-2.0 pg/ml Flt-3, about 9.5-16 pg/ml PDGF-AA, about 0.65-1.035 ng/ml TGF-β1, about 28-46 pg/ml TGF-β3, and about 85-130 pg/ml TGF-β2. The amount of growth factors in the media or composition may be determined by standard methods known in the art (for example, but not limited to, ELISA).

In embodiments, a method is disclosed including administering to a subject in need thereof a composition formulation derived from conditioned media containing vesicles. In a related aspect, the vesicles are exosomes. The exosomes may contain various cell-derived components such as protein, DNA, or RNA (e.g., a miRNA). In embodiments, the proteins included may be characteristic of exosomes. For example, the vesicles may contain TSG101 and CD63 proteins or the vesicles may contain CD34+ protein. Other proteins include, but are not limited to, EGF, PDGF, FGF, TGF-β, TGF-α, NGF, Epo, IGF-I, IGF-II, IL-1-α, IL-1-β, IL-2, IL-3, IL-4, IL-5, IL-6, IL-7, IL-8, IL-9, IL-10, IL-11, IL-12, IL-13, INF-α, INF-β, INF-γ, TNF-a, TNF-β, GM-CSF, and M-CSFs, or combinations thereof. Moreover, exosome compositions may comprise ALIX or PDCD6IP, RABGTpases, annexins, cytoskeletal proteins, adhesion molecules and tetraspanin family proteins. In embodiments, specific lipid compositions may be contained in said exosomes, including but not limited to, cholesterol, ceramide and sphingolipids.

In embodiments, a method of making a composition is disclosed including culturing a first substantially homogenous set of cells; harvesting the medium conditioned by the first set of cells; optionally, culturing a second substantially homogenous set of cells; harvesting the medium conditioned by the second set of cells; isolating exosomes from the conditioned medium of the first or second set of cells; adding the isolated exosomes to the conditioned medium from the first or second set of cells to form a conditioned medium containing an enriched population of exosomes; and adding the conditioned medium containing the enriched population of exosomes to a formulation comprising one or more components to form ophthalmic composition.

In addition, cells also produce exosomes which contain functional mRNA, miRNA, DNA, and protein molecules that may be taken up by target cells. The molecules contained in exosomes can influence target cell activation, migration, growth, differentiation or de-differentiation, or promote apoptosis or necrosis. As such, conditioned media enriched in exosomes may be used to provide additional cell factors that assist in treating, e.g., dry eye.

In addition, exosome production may be induced/enhanced in corneal epithelial cells by cytokine/mitogen exposure, uptake of latex beads, $Ca^{+2}$ exposure, hypoxia, or other manipulations of the cell culture (e.g., apoptosis induction).

After conditioned media is isolated, exosomes may be extracted from media by methods know in the art (see, e.g., Taylor et al., Methods in Mol. Biol. 728:235-246, 2011).

In embodiments, the conditioned media may be centrifuged at 12,000×g for about 15 min. at about 4° C. (low speed centrifugation). The resulting supernatant may then be centrifuged at 100,000×g for about 1 hr at about 4° C. The resulting pellet may then be re-suspended in 4° C. phosphate buffered saline (i.e., PBS; other physiological buffers may be used), and the re-suspended material may then be re-centrifuged for 1 hr at 100,000×g, 4° C., and resuspended in PBS until use.

In embodiments, the exosomes may be isolated by column chromatography. As stated above, the conditioned media may be centrifuged at 12,000×g for about 15 min. at about 4° C. After low speed centrifugation, an aliquot of the supernatant (e.g., 2-3 ml) is applied to a 2% agarose based gel column (2.5×16 cm). For optimum separation, the sample volume should be about $\frac{1}{20}$ of the total column volume (as defined by $\Pi r^2 h$). The material may then be eluted isocratically with PBS at a flow rate of about 1 ml/min, monitoring the eluate at 280 nm, where fractions are collected (2-3 ml). The void volume fractions are pooled, and centrifuged at 100,000×g for 1 hr at 4° C., where the pelleted exosomes may be recentrifuged after suspension in PBS, and finally resuspended in PBS until use.

Alternatively, populations of exosomes may be enriched by absorption to antibody conjugated magnetic microbeads. For example, anti-surface-antigen Ab-magnetic beads (about 50 µl) may be mixed with about 2 ml of low speed centrifugation conditioned media supernatant, and incubated on a shaker at room temperature. After a sufficient time (about 2 hrs), tubes containing the immune complexes are place in a magnetic separator, the fluid is removed, leaving the magnetic beads (mb) and bound exosomes attached to the side of the tubes. The tubes may then be removed from the magnetic separator, where the beads are rinsed with about 500 µl of Tris buffered saline (although other buffers may be used) and the separation repeated. The isolated exosomes/microbeads may be diluted in IgG elution buffer (Pierce Chemical Co, Rockford, Ill.) and the complex centrifuged at about 10,000 rpm (low speed centrifuge) to separate the microbeads from the exosomes (supernatant). The supernatant may then be centrifuged at 100,000×g for about 1 hour at 4° C. The pelleted exosomes may then be resuspended in about 250 µl phosphate-buffered saline (PBS).

Other methods include the use of EXOQUICK™ (300-500 mg/ml polyethylene glycol (PEG), 400-8000 Daltons, in phosphate buffered saline (PBS), pH 7.4) (available from System Biosciences Inc, Mountain View, Calif.; see Taylor et al. (2011), supra) polymer based precipitation methods.

Once isolated, the exosomes may be analyzed for protein/RNA analysis or may be used to form the formulations as disclosed herein. In a related aspect, the formulations may contain about 5-40% conditioned medium, about 10-38% conditioned media, about 25-35% conditioned media, where the conditioned medium contains at least about a 20% increase in exosomes, about a 40% increase in exosomes, about a 50% to about a 100% increase in exosomes, about a 1.5 fold increase in exosomes, about 1.5 to about 2.5 fold increase in exosomes, about 2.5 to about 3.5 fold increase in exosomes, about 3.5 to about 4.5 fold increase in exosomes, about 5 fold increase in exosomes or about a 10 fold increase in exosomes compared to non-enriched conditioned media.

In embodiments, conditioned media contains about 1.5 to about 10 fold more exosomes compared to non-enriched conditioned media.

The conditioned medium may be formulated into a topical ophthalmic composition as disclosed for preventing, reducing and/or eliminating epithelial lesions of the eye or ophthalmic disorders.

In one embodiment, the conditioned cell medium may be formulated as a drop, and/or serum for topical application, with or without additional growth factors, peptides, and/or other proteins and biologically active substances, including, but not limited to, those discussed herein.

In addition to the other active agents discussed above, typical topical ophthalmic composition formulations may include one of more components as described herein.

Aqueous ophthalmic compositions may be formulated, for example, in accord with the procedures set forth in Chapter 83 of Remington's Pharmaceutical Sciences, 14th Edition, Mack Publishing Company. As such, they are sterile and may contain bacteriological preservatives to maintain sterility during use.

For most purposes, the addition of benzalkonium chloride to the ophthalmic composition provides the desired biocidal preservative effect. However, additional biocides may be incorporated, if desired. For example, it is generally desirable to incorporate a suitable chelating agent to enhance the preservative effect of the benzalkonium chloride. Suitable chelating agents include di-, tri-, or tetrasodium ethylene diamine tetracetate, also known as edetates, with disodium edetate being a preferred ingredient. Other biocides that may be optionally included in the ophthalmic composition include thimerosal, phenylmercuric nitrate, chlorobutanol, and sorbicacid.

For some purposes, the ophthalmic composition may comprise one or more antibiotics, for example, including but not limited to, bacitracin, neomycin, gentamicin, tobramycin, ciprofloxicin, cefazolin, chloramphenicol, ofloxicin, vancomycin, ceftazidime, and amikacin or a combination thereof. In one aspect, the ophthalmic composition comprises bacitracin and neomycin.

For most ophthalmic uses it is desirable that the ophthalmic composition be isotonic. Conventionally, ophthalmic compositions are rendered isotonic by addition of suitable salts, for example, sodium chloride, potassium chloride, calcium chloride, magnesium chloride, and various nitrates, citrates, acetates, and the like. In one aspect, monovalent salts such as sodium chloride and the like are added in an amount sufficient to give a freezing point depression or osmotic pressure equivalent to that provided by about 0.5%-1.5% sodium chloride. Such compositions may also comprise bicarbonate.

If desired, the ophthalmic composition utilized in this invention may be adjusted in pH by one or more of the acids or bases known for use in ophthalmic compositions. The ophthalmic compositions may be maintained in an acidic, basic, or neutral condition by use of buffers commonly employed in ophthalmic solutions. The use of suitable acids, bases and buffering systems to establish a pH within the range of from about 3.0-8.5 is well known and requires no further description. Typically, the pH of the ophthalmic solutions utilized in this invention is between about 5.0-8.0, preferably between about 6.0-7.5.

The viscosity of the ophthalmic compositions used in the present invention may be adjusted to a point within the range of from about 1 cps to about 25 cps at 25° C. (The viscosity of the ophthalmic solutions are measured on a Wells-Brookfield Microviscometer (cone and plate) Model LVT). Such an adjustment can be made by inclusion of water-soluble viscosity building agents. Suitable viscosity building agents include natural gums, such as guar gum and gum tragacanth; gelatin; starch derivatives; polymeric glycols; and cellulosic polymers, such as hydroxyethylcellulose, hydroxypropylcellulose, methylcellulose, hydroxyropylmethylcellulose, and carboxymethylcellulose (CMC). Viscosity building agents, when used, are present in such ophthalmic compositions at a level of from about 0.001% to about 1.0% by weight. The exact percentage depends on the molecular weight of the polymer used which is within the skill of the art. When a viscosity building agent is utilized, the viscosity of the ophthalmic compositions may be between about 1 cps and about 25 cps, preferably between about 3 cps-5 cps.

In one embodiment, the formulated topical ophthalmic composition combines therapeutically effective amounts of conditioned medium (or concentrates or extracts thereof) with a viscosity builder, purified water, and at least one preservative.

In a related aspect, the builder comprises carboxymethylcellulose or methylcellulose, or polyvinylpyrrolidone or a polyacrylic acid polymer or copolymer.

Therapeutic products contained in the conditioned media include, but are not limited to, peptides, growth factors, enzymes, hormones, cytokines, antigens, antibodies, clotting factors, and regulatory proteins. Of course, the medium may be further processed to concentrate or reduce one or more factor or component contained within the medium, for example, enrichment of a growth factor using immunoaffinity chromatography or, conversely, removal of a less desirable component.

Alternatively, the conditioned cell medium may be formulated with polymerizable or cross-linking hydrogels as described in U.S. Pat. Nos. 5,709,854; 5,516,532; 5,654,381; and WO 98/52543, each of which is incorporated herein by reference in its entirety. Examples of materials which can be used to form a hydrogel include modified alginates. Alginate is a carbohydrate polymer isolated from seaweed, which can be cross-linked to form a hydrogel by exposure to a divalent cation such as calcium, as described, for example in WO 94/125080, the disclosure of which is incorporated herein by reference. Alginate is ionically cross-linked in the presence of divalent cations, in water, at room temperature, to form a hydrogel matrix. As used herein, the term "modified alginates" refers to chemically modified alginates with modified hydrogel properties.

Additionally, polysaccharides which gel by exposure to monovalent cations, including bacterial polysaccharides, such as gellan gum, and plant polysaccharides, such as carrageenans, may be cross-linked to form a hydrogel using methods analogous to those available for the cross-linking of alginates described above.

Modified hyaluronic acid derivatives may also be useful. As used herein, the term "hyaluronic acids" refers to natural and chemically modified hyaluronic acids. Modified hyaluronic acids may be designed and synthesized with preselected chemical modifications to adjust the rate and degree of cross-linking and biodegradation.

Covalently cross-linkable hydrogel precursors also are useful. For example, a water soluble polyamine, such as chitosan, can be cross-linked with a water soluble diisothiocyanate, such as polyethylene glycol diisothiocyanate.

Alternatively, polymers may be utilized which include substituents which are cross-linked by a radical reaction upon contact with a radical initiator, such as those disclosed in Naughton et al., U.S. Pat. No. 6,372,494, herein incorporated by reference in its entirety.

In one embodiment, a contact lens may be used to deliver the ophthalmic composition to a subject in need thereof. For example, soft contact lenses may be used to encapsulate the ophthalmic formulations of the present invention using nanoparticles which may be dispersed throughout the contact lens matrix. See, e.g., Chauhan et al., U.S. Pat. No. 7,638,137, herein incorporated by reference in its entirety. Alternatively, the formulations may be coated onto a lens surface by passive transfer. See, e.g., Schultz et al., U.S. Pat. No. 6,410,045, herein incorporated by reference in its entirety. Other methods for delivering various medicaments using contact lenses can be found in U.S. Pat. Nos. 4,617,299; 4,668,506, 5,212,168 and 5,723,131, the teachings of which are herein incorporated by reference.

In another embodiment, the present invention includes a kit. Such kits may include, but are not limited to, at least one container, an ophthalmic composition comprising conditioned media or extract or concentrate thereof from cultured conjunctiva cells and a water-soluble viscosity building agent, instructions which provide methods of mixing the composition and water-soluble building agent and/or methods of applying the composition to treat or prevent dry-eye, and optionally, a label. The container may be used to mix the conditioned media and the viscosity building agent, where the proportions of media to viscosity building agent are varied to modulate the dose delivered to the eye. In a related aspect, the container may contain contact lenses, and the proportions of media to viscosity binding agent are varied to modulate the amount of therapeutic agent which passively transfers to the lens. The instructions may be a pamphlet, CD, or other computer readable medium. Further, the instructions may provide information about a website which may contain downlodable content.

The ophthalmic composition described herein may be administered once, twice, three times, four times, or five times each day, or in other quantities and frequencies. Alternatively, the ophthalmic composition may be administered once per week, twice per week, three times per week, four times per week, five times per week, or six times per week. Therapy with the composition described herein can continue until the epithelial lesion has healed or the ophthalmic disorder has been ameliorated. The duration of therapy can be, e.g., one week to one month; alternatively, the pharmaceutical composition can be administered for a shorter or a longer duration. Continuous daily dosing with compositions used in the methods described herein may or may not be required. A therapeutic regimen may require cycles, during which time a composition is not administered, or therapy may be provided on an as-needed basis.

Appropriate dosages of compounds used in the methods described herein depend on several factors, including the administration method, the severity of the epithelial lesion or disorder, and the age, weight, and health of the patient to be treated. Additionally, pharmacogenomic information (e.g., the effect of genotype on the pharmacokinetic, pharmacodynamic, or efficacy profile of a therapeutic) about a particular patient may affect the dosage used.

Assays commonly employed by those of skill in the art may be utilized to test the activity of the particular factor or factors, thereby ensuring that an acceptable level of biological activity (e.g., a therapeutically effective activity) is retained and/or generated by post-harvest processing. Doses of such therapeutic factors are well known to those of skill in the art and may be found in pharmaceutical compedia such as the PHYSICIANS DESK REFERENCE, Medical Economics Data Publishers; REMINGTON'S PHARMACEUTICAL SCIENCES, Mack Publishing Co.; GOODMAN & GILMAN, THE PHARMACOLOGICAL BASIS OF THERAPEUTICS, McGraw Hill Publ., THE CHEMOTHERAPY SOURCE BOOK, Williams and Wilkens Publishers.

The therapeutically effective doses of any of the growth factors, drugs or other active agents described above may routinely be determined using techniques well known to those of skill in the art. In one aspect of the present invention, the amount of mucin in a dose of the ophthalmic composition is about 0.0005-0.001% (w/v) in a volume of about 0.1 ml.

Therapy according to the methods described herein may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the severity of the patient's epithelial lesion or ophthalmic disorder, and how the patient responds to the treatment.

In order to measure the efficacy of any of the methods or compositions described herein, a pain measurement index may be used. Indices that may be useful in the methods and compositions described herein include a visual analog scale (VAS) or a Likert scale, each of which is well-known in the art. Such indices may be used to measure pain, tenderness, light sensitivity, itchiness, burning sensations, eye-pain sensations, or other variables.

A visual analog scale (VAS) provides a measure of a one-dimensional quantity. A VAS generally utilizes a representation of distance, such as a picture of a line with hash marks drawn at regular distance intervals, e.g., ten 1-cm intervals. For example, a patient can be asked to rank a sensation of pain by choosing the spot on the line that best corresponds to the sensation of pain, where one end of the line corresponds to "no pain" (score of 0 cm) and the other end of the line corresponds to "unbearable pain" (score of 10 cm). This procedure provides a simple and rapid approach to obtaining quantitative information about how the patient is experiencing pain. VAS scales and their use are described, e.g., in U.S. Pat. Nos. 6,709,406 and 6,432,937, the teachings of which are herein incorporated by reference.

A Likert scale similarly provides a measure of a one-dimensional quantity. Generally, a Likert scale has discrete integer values ranging from a low value (e.g., 0, meaning no pain) to a high value (e.g., 7, meaning extreme pain). A patient experiencing pain is asked to choose a number between the low value and the high value to represent the degree of pain experienced. Likert scales and their use are described, e.g., in U.S. Pat. No. 6,623,040 and U.S. Pat. No. 6,766,319, the teachings of which are herein incorporated by reference.

Alternatively, efficacy of the present compositions may be made using microscopy; e.g., to determine corneal healing by examining the corneal/ocular curve and anatomy using confocal and/or slit lamp microscopy. The use of confocal microscopy to determine corneal healing is well known in the art, e.g., Patel et al., Invest Ophthal Visual Sci (2001) 42:333-339, as is slit lamp microscopy, e.g., Waring et al., Am J Ophthalmol (1985) 100(1):218-224, each of which is incorporated by reference.

The following examples are intended to illustrate but not limit the invention.

EXAMPLES

Example 1

Preparation of the Ophthalmic Composition

The anterior segment of the eye was removed under sterile conditions by a circular incision through the sclera 2 mm below the limbus. The segment was carefully transferred into a dish containing Dulbecco's modified Eagles medium (DMEM), supplemented with 3% foetal calf serum (FCS), 50 mg/ml of gentamicin and 5 mg/ml of amphotericin B. The iris-ciliary body, lens, and corneal endothelium were removed microscopically. The resulting specimen was dissected into three zones; i.e., the central cornea, peripheral cornea and limbus, and freed of any adhesive tissue fragments. 5 ml of 0.25% trypsin EDTA was added and the resulting mixture was incubated at 37° C. After incubation of 1 hr, both the central and peripheral corneal specimens were centrifuged at 800×g for 10 min (rotating compact centrifuge 6×10/15 ml angle rotor). The epithelial sheets were resuspended in 0.25% trypsin and EDTA for 10 minutes with intermittent gentle shaking. Enzymatic digestion was halted with the addition of DMEM containing 3% FCS. The three isolated cell types were cultured in both Epi-Life Media (Cascade Biologic) and DMEM containing 3% FCS and antibiotics. The cultures were incubated at 37° C., 95% humidity, and 5% $CO_2$. The media was changed every 2 days to every 6 days, depending on type of media used. Cells were either further cultured or processed for freezing at 60-70% confluence. The supernatant was removed from the cultured cells (i.e., conditioned media) for the ophthalmic composition formulation when the cells reached about 95-100% confluency. Homogenous cell population prepared by this method were deposited in the ATCC, having Accession No. PTA-120527.

When cells reached about 80-95% confluence, the conditioned media was then used for exosome isolation.

Exosome Isolation

The conditioned media was centrifuged at 12,000×g for about 15 min. at about 4° C. (low speed centrifugation). The resulting supernatant was then centrifuged at 100,000×g for about 1 hr at about 4° C. The resulting pellet was then re-suspended in 4° C. phosphate buffered saline, and the re-suspended material was then re-centrifuged for 1 hr at 100,000×g, 4° C.

This resulted in about 1-4 μg exosomes/ml culture from the media, as determined by ELISA or FACS.

When sufficient exosomes were isolated to achieve at least about a 20% increase above the exosome population in the non-enriched culture was obtained, they were resuspended in conditioned media (about 1-5 ml), and added to the composition as set forth below.

The conditioned media or conditioned media containing an enriched exosome fraction was formulated into a topical ophthalmic composition as follows: 6.25 gm of CMC was blended with Ringers for 30-60 minutes. The resulting suspension was poured into non-sterile serum bottles. The bottles were capped and autoclaved for 20 minutes at 121° C. The autoclaved suspension was combined with the cell supernatant, where the cell supernatant was added to final concentration of about 60-65% (v/v). The final composition was then transferred to 5 ml bottles.

Example 2

Treatment of Human Subjects Exhibiting Dry Eye with the Conditioned Media-Containing Ophthalmic Composition The ophthalmic composition was formulated as above as an isotonic aqueous solution and topically administered to the eyes of human subjects and visual analog scale (VAS) studies were conducted as a measure of efficacy of the composition in subjects with dry-eye.

19 otherwise healthy, (7 males, 12 females), adult volunteers (ranging in age from 31-53) exhibiting dry eye were used for these studies. Volunteers signed comprehensive informed consent documents.

The subjects were dosed at one drop (about 0.1 ml) instilled 2 times a day into the eye of the subjects for 30 days. Subjects were followed for up to 2 years after treatment.

As illustrated in FIG. 1, subjects treated with the conditioned media-containing ophthalmic solution (GF-AG-Ophtho; bar 4) showed at least a four-fold improvement relative to placebo (bar 1), RESTASIS™ (0.05% cyclosporine ophthalmic emulsion) (bar 3) or artificial tears (bar 4). Further, subjects reported no symptoms following the use of the conditioned media containing ophthalmic composition.

Example 3

Subjects Exhibiting Corneal Lesions Treated with the Conditioned Media-Containing Ophthalmic Composition The ophthalmic composition was formulated as above as an isotonic aqueous solution, except that bacitracin+neomycin was added to achieve a final concentration of 500 mg/dose. The composition was topically administered to the eyes of human subjects and assessment was made using ophthalmic eye surgery microscopy.

13 otherwise healthy, (8 males, 5 females), adult volunteers (ranging in age from 31-53) exhibiting corneal lesions were used for these studies. Volunteers signed comprehensive informed consent documents.

The subjects were dosed at one drop (about 0.1 ml) instilled 4 times a day into the eye of the subjects for 1 week.

Figure 2:
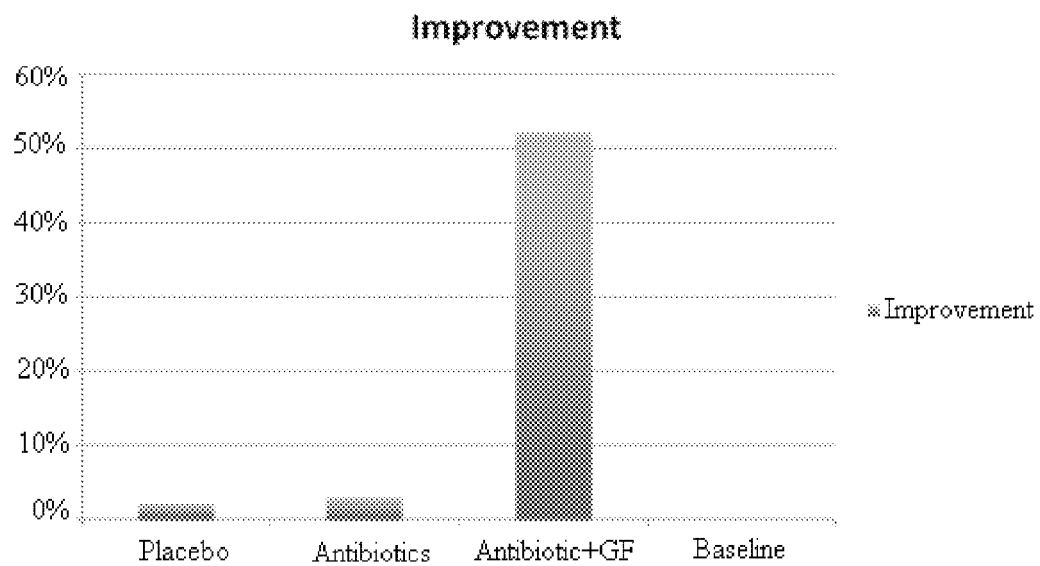
FIG. 2 shows the improvement in healing of corneal lesions in patient receiving GF-AG-Ophtho+antibiotics (bar 3). Treatment was compared to placebo (bar 1), antibiotics alone (bacitracin+neomycin; bar 2), and baseline (no treatment).

As illustrated in FIG. 2, subjects treated with GF-AG-Ophtho (bar 4) showed at least a ten-fold improvement relative to antibiotics alone as assessed by slit lamp microscopy.

It should be understood that the invention is not limited to the embodiments set forth herein for purposes of exemplification, but is to be defined only by a fair reading of the appended claims, including the full range of equivalency to which each element thereof is entitled. Although the invention has been described with reference to the above examples, it will be understood that modifications and variations are encompassed within the spirit and scope of the invention. Accordingly, the invention is limited only by the following claims.

I claim:

1. A human corneal epithelial cell line, wherein the cell line has an ATCC Accession No. PTA-120527.

* * * * *